(12) United States Patent
Hu et al.

(10) Patent No.: US 9,989,481 B2
(45) Date of Patent: Jun. 5, 2018

(54) RAPID MICROWAVE PHASE DETECTION WITH A SOLID STATE DEVICE

(71) Applicant: UNIVERSITY OF MANITOBA, Winnipeg (CA)

(72) Inventors: Can-ming Hu, Winnipeg (CA); Yongsheng Gui, Winnipeg (CA); Lei Fu, Winnipeg (CA)

(73) Assignee: University of Manitoba, Winnipeg (CA)

( * ) Notice: Subject to any disclaimer, the term of this patent is extended or adjusted under 35 U.S.C. 154(b) by 11 days.

(21) Appl. No.: 15/030,548

(22) PCT Filed: Sep. 26, 2014

(86) PCT No.: PCT/IB2014/002814
§ 371 (c)(1),
(2) Date: Apr. 19, 2016

(87) PCT Pub. No.: WO2015/063596
PCT Pub. Date: May 7, 2015

(65) Prior Publication Data
US 2016/0266052 A1    Sep. 15, 2016

Related U.S. Application Data

(60) Provisional application No. 61/897,653, filed on Oct. 30, 2013.

(51) Int. Cl.
*G01N 22/00* (2006.01)
*G01R 29/08* (2006.01)

(52) U.S. Cl.
CPC ......... *G01N 22/00* (2013.01); *G01R 29/0814* (2013.01); *G01R 29/0871* (2013.01)

(58) Field of Classification Search
CPC ........ G01N 22/00; G01N 22/04; G01N 22/02; G01N 22/005; G01R 27/04; G01R 29/08
See application file for complete search history.

(56) References Cited

U.S. PATENT DOCUMENTS

| 5,767,685 A | 6/1998 | Walker ..................... 324/640 |
| 2012/0001656 A1 | 1/2012 | Hu et al. ..................... 327/3 |

OTHER PUBLICATIONS

Yao et al, Rapid microwave phase detection based on a solid state spiontronic device, Sep. 13, 2013, Arxiv.org, APS-123-QED, pp. 1-5.*

(Continued)

*Primary Examiner* — Jermele M Hollington
*Assistant Examiner* — Suresh K Rajaputra
(74) *Attorney, Agent, or Firm* — Norton Rose Fulbright US LLP

(57) ABSTRACT

A solid state sensor may be used to down-convert microwave signal into a low-frequency voltage or current signal, where its phase still carries the information of a measured continuous wave (CW) microwave phase. Two CW microwaves may be mixed and a solid state sensor used to rectify the mixed microwave into a direct voltage or current signal. The measurement system may include an input node for receiving a microwave signal from a source from which the output microwave is coherently split into two parts by a microwave power divider. Each part may travel in a separate path and couple at the solid state sensor. A lock-in amplifier coupled to the solid state sensor may be used to determine simultaneously a magnitude and phase of the microwave signals received from the microwave source.

24 Claims, 7 Drawing Sheets

(56) References Cited

OTHER PUBLICATIONS

International Preliminary Report on Patentability issued in Application No. PCT/IB2015/002814, dated May 12, 2016.
International Search Report and Written Opinion issued in Application No. PCT/IB2014/002814, dated Mar. 25, 2015.
Xin et al., "Microwave phase detection with a magnetic tunnel junction," *Applied Physics Letters 97.21* , AIP Publishing, 2010.

* cited by examiner

RAPID MICROWAVE PHASE DETECTION WITH A SOLID STATE DEVICE

CROSS-REFERENCE TO RELATED APPLICATIONS

This application is a national phase application under 35 U.S.C. § 371 of International Application No. PCT/IB2014/002814, filed Sep. 26, 2014, which claims the benefit of priority of U.S. Provisional Application No. 61/897,653 to Hu et al. entitled "Rapid Microwave Phase Detection with Solid State Devices" filed. Oct. 30, 2013, all of which applications are hereby incorporated by reference in their entireties.

FIELD OF THE DISCLOSURE

This disclosure relates to methods and apparatuses for measuring microwave signals, and more particularly to sensors for detecting microwave signals.

BACKGROUND

Measurement of microwave signals, such as continuous wave (CW) microwaves, is an integral part of many theoretical experiments and commercial systems. For example, CW microwave measurements are involved in ground penetrating detection, non-destructive testing and medical imaging. Analyzing the phase information of the microwave signals is important for estimating electric permittivity and conductivity profiles of measured materials or medical samples. However, traditional time-domain microwave sensing systems employ complicated equipment, such as vector network analyzers (VNAs), to measure in-phase and quadrature components of a microwave signal received at an antenna. Such a conventional system is shown in FIG. 1.

FIG. 1 is block diagram illustrating a conventional system for measuring microwave signals. A system 100 may include an antenna 102 coupled to a vector network analyzer 104, which may provide signals to a personal computer 106 for analysis and storage. However, the vector network analyzer 104 is an expensive and complicated tool that is difficult for use without extensive training.

One conventional solution is the use of solid state devices such as a spintronics or a semiconductor sensor to detect microwave signals and obtain phase information regarding the microwave signals. However, solid state devices in conventional setups take far longer to complete a phase measurement compared to a system using a vector network analyzer, such as the system 100 of FIG. 1. That is because with a solid state device, an operator must tune a phase shifter through a series of values and perform a computer fitting of the measured alternating interference fringes of rectified voltage in order to determine phase information of the microwave signal.

BRIEF SUMMARY

Measurement of microwave signals may be improved using spintronic devices, and other solid state devices, to allow rapid measurement of magnitude and phase information of a microwave signal. In one embodiment, the measurement of magnitude and phase may be performed simultaneously with a solid state sensor. A lock-in amplifier may be coupled to the solid state sensor and used to perform real-time microwave measurement through the solid state sensor. The solid state sensor may be, for example, a nano-structured spintronic device.

A solid state sensor may be used to down-convert a microwave signal into a low-frequency voltage or current signal, where its phase still carries the information of a measured CW microwave phase. Two CW microwaves may be mixed and a solid state sensor used to rectify the mixed microwave into a direct voltage or current signal. The measurement system may include a microwave source (emitting CW microwaves with a frequency of $\omega$) from which the output microwave may be coherently split into two parts by a microwave power divider. Each part may travel in a separate path and couple at the solid state sensor. At the sensor, the second microwave signal (reference path) may have a phase of $\varphi_0$ as well as a periodic-time-dependent phase shift of $\omega_r t$ ($\omega_r \ll \omega$), while the first microwave signal (testing path) may have a phase of $\varphi$. The mixing of the two microwaves may follow a relation of $\cos(\omega t+\varphi)\cos(\omega t=\omega_r t+\varphi_0)=[\cos(2\omega t+\omega_r t+\varphi+\varphi_0)+\cos(\omega_r t+\varphi_0-\varphi)]/2$, and may result in a second harmonic microwave signal with a form of $\cos(2\omega t+\omega_r t+\varphi+\varphi_0)$ and a low frequency signal with a form of $\cos(\omega_r t+\varphi_0-\varphi)$. Through the rectification of solid state sensors, a low frequency signal of $V(t)=V_0 \cos(\omega_r t+\varphi_0-\varphi)$ may be generated, in which $V_0$ depends on the amplitudes of the input microwave signals. Thus, the microwave phase shift of $(\varphi-\varphi_0)$ may be determined by comparing with a standard low-frequency wave of $\cos(\omega_r t)$.

According to one embodiment, an apparatus may include a solid state sensor configured to receive a first microwave signal and a second microwave signal. The apparatus may also include a lock-in amplifier coupled to the solid state sensor. The apparatus may further include a voltage-controlled phase shifter coupled to the solid state sensor and configured to provide the phase-modulated second microwave signal. The apparatus may also include a function generator coupled to the voltage-controlled phase shifter.

According to another embodiment, a method may include receiving a first microwave signal at a solid state sensor. The method may also include generating a second microwave signal phase-modulated by a voltage-controlled phase shifter. The method may include combining first and second microwave signals at the solid state sensor to generate a low frequency signal. This generated low frequency signal having an amplitude proportional to an amplitude of the first microwave signal and having a phase with a defined relationship with the first microwave signal. The method may also include measuring the low frequency signal at the solid state sensor with a lock-in amplifier According to a further embodiment, a system may include an array of solid state sensors configured to receive a first microwave signal and a second microwave signal. The system may also include a lock-in amplifier coupled to the array of solid state sensors. The system may further include a voltage-controlled phase shifter coupled to the solid state sensors and configured to provide the second microwave signal. The system may also include a function generator coupled to the voltage-controlled phase shifter.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features that are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments.

DETAILED DESCRIPTION

Figure 1:
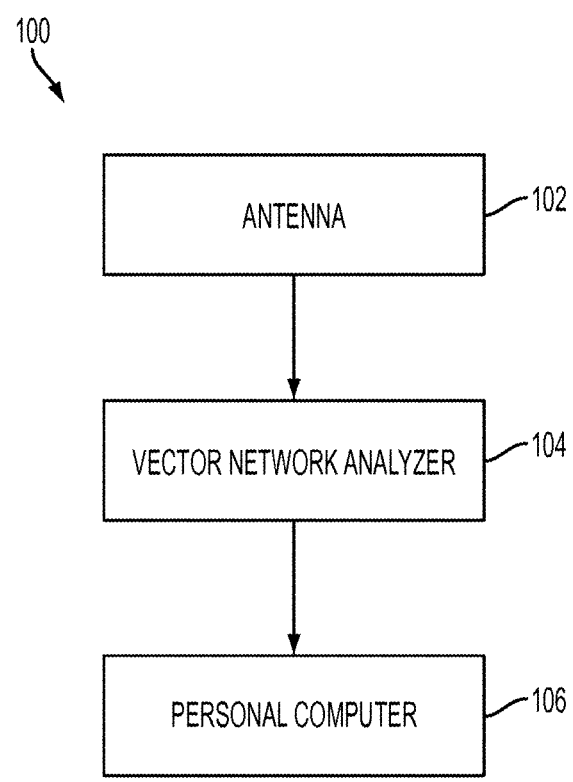
FIG. 1 is a block diagram illustrating a conventional system for measuring microwave signals.
Figure 2:
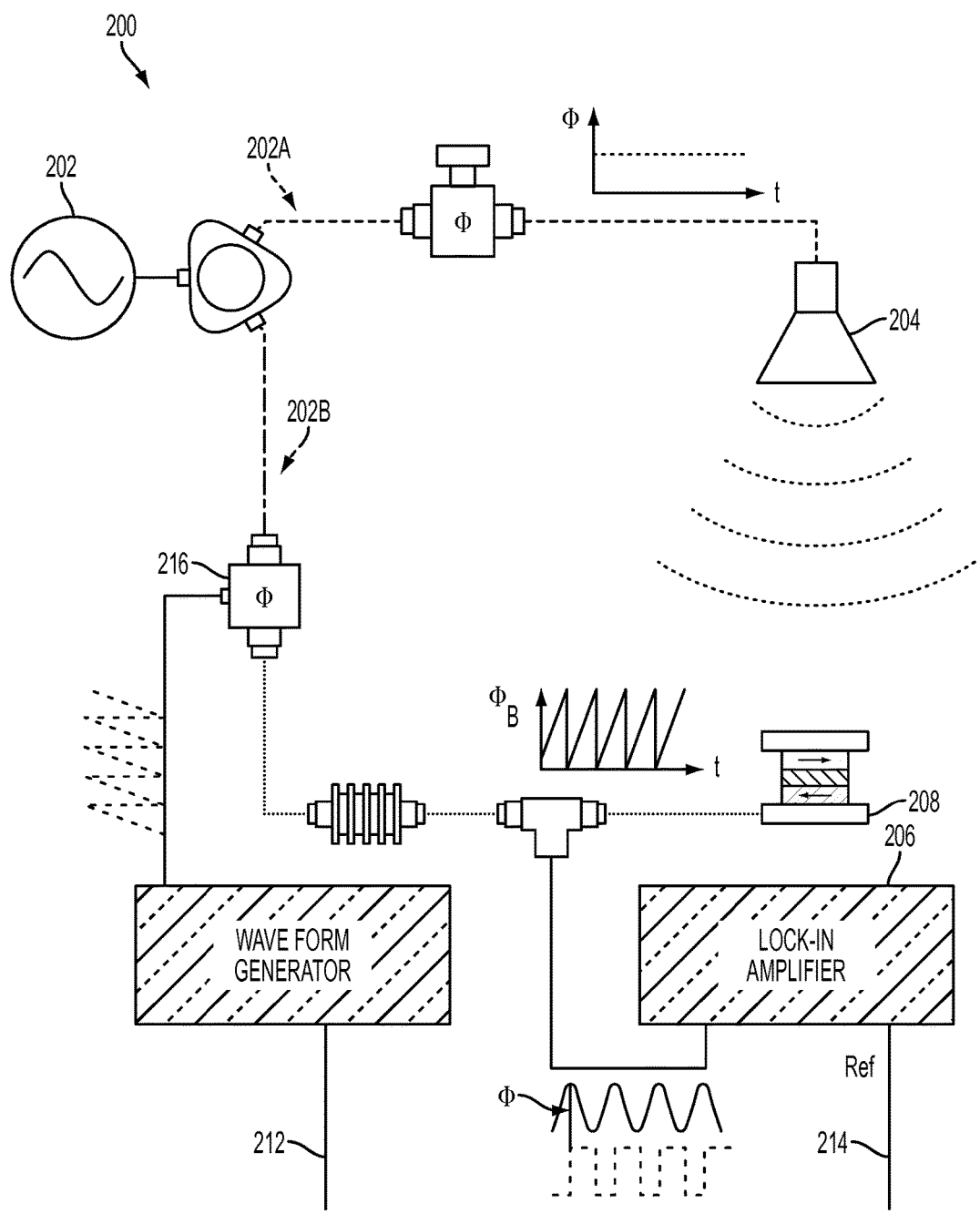
FIG. 2 is a block diagram illustrating a system for measuring microwave signals with a solid state sensor according to one embodiment of the disclosure.

Rapid detection of microwave signal phase information with a solid state sensor may be performed with a lock-in amplifier, such as shown in the system of FIG. 2. FIG. 2 is a block diagram illustrating a system for measuring microwave signals with a solid state sensor according to one embodiment of the disclosure. A system 200 may include an RF source 202 coupled to a first path 202A and a second path 202B. The source 202 may be an generated microwave signal, such as from an RF generator, or a received microwave signal, such as from an antenna. A microwave signal from the source 202 may be coherently split into two parts by a microwave power divider, and each part travel along the paths 202A and 202B before both paths couple at a solid state sensor.

The first path 202A may include, for example, an SMA to wave guide adapter, a horn antenna 204, coaxial cables, and/or other items (not shown). The RF source 202 may also be coupled to a second path 202B including, for example, a voltage-controlled phase shifter 206, an adjustable attenuator for balancing the strength of the two microwave signals, a bias tee for separating RF and low frequency signals, a solid state sensor 208, coaxial cables, and/or other items (not shown). Control components may be coupled to the path 202B to control measurement of microwave signals at the solid state sensor 208 including, for example, a wave form generator 212 and/or a lock-in amplifier 206. The solid state sensor 208 may, therefore, receive two microwave signals: a first microwave signal transmitted by the horn 204 to be measured by the solid state sensor 208, and a second microwave signal transmitted along the path 202B.

The solid state sensor 208 may include one or more of a number of devices having either one or multiple layers, including a magnetic tunnel junction (MTJ), a Schottky diode, and/or a metal-insulator-metal (MIM) diode. The microwave signals may generate a voltage on the solid state sensor 208 that is measurable with the lock-in amplifier 206. For example, in a magnetic tunnel junction (MTJ), the microwave fields may be rectified in the absence of an external field through the Seebeck rectification and/or other effects. In one embodiment, the MTJ may include for example a tri-layer structure (e.g., CoFeB/MgO/CoFeB) of Ferromagnetic metal (CoFeB), Magnesium Oxide (MgO), and Ferromagnetic metal (CoFeB). The I-V characterization of an MTJ is in general non-linear, which can be caused by many reasons including thermal Seebeck effect. Under microwave radiation, this nonlinearity of the MTJ produces microwave rectification.

The first microwave signal may be detected by applying the second microwave signal through the path 202B and adjusting the phase with the voltage-controlled phase shifter 216. Adjusting the phase with the phase shifter 216 may allow a microwave sensor, such as the solid state sensor 208, to simultaneously determine the magnitude and phase of microwave signals. The phase shifter 216 may be controlled through application of a signal from, for example, a function generator that produces a sawtooth wave at a frequency of $\omega_V$, which may be much smaller than $\omega$, the frequency of the microwave source 202. The range of voltage bias may be set to vary the phase delay from 0 to 360 degrees. Thus, the microwave phase for the path 202B may be given by $$\varphi_B(t) = \omega_V t + \varphi_0,$$

where $\varphi_0$ is an initial phase of the second microwave signal of path 202B. The voltage generated across the solid state sensor 208, such as a magnetic tunnel junction (MTJ), due to the mixing of two microwaves, may be given by $$V \propto [e_T e_R \cos(2\omega t + \omega_V t + \varphi + \varphi_0) + e_T e_R \cos(\omega_V t + \varphi_0 - \varphi)]/2,$$

where $e_T$ is a magnitude of the first microwave signal of path 202A and $e_R$ is a magnitude of the second microwave signal of path 202B. This may produce a second harmonic microwave signal with a frequency of approximately $2\omega$, which may be undetectable by the lock-in amplifier, and a low frequency signal proportional to $$\cos(\omega_V t + \varphi_0 - \varphi),$$

which can be measured by the lock-in amplifier, where $\varphi$ is a phase of the first microwave signal of path 202A.

The phase information, $\varphi$, of the first microwave signal of path 202A may be measured with the lock-in amplifier 206, or other digital signal processor, triggered by a reference signal 214 such as, for example, a square wave. The reference signal 214 may be synchronized with the function generator controlling the phase shifter 216. In one embodiment, the lock-in amplifier 206 may detect both an in-phase and a quadrature component of the voltage signal across the solid state sensor 208 varying with a frequency of approximately $\omega_r$. Thus, the phase shift, $\varphi-\varphi_0$, may be measured.

Figure 3:
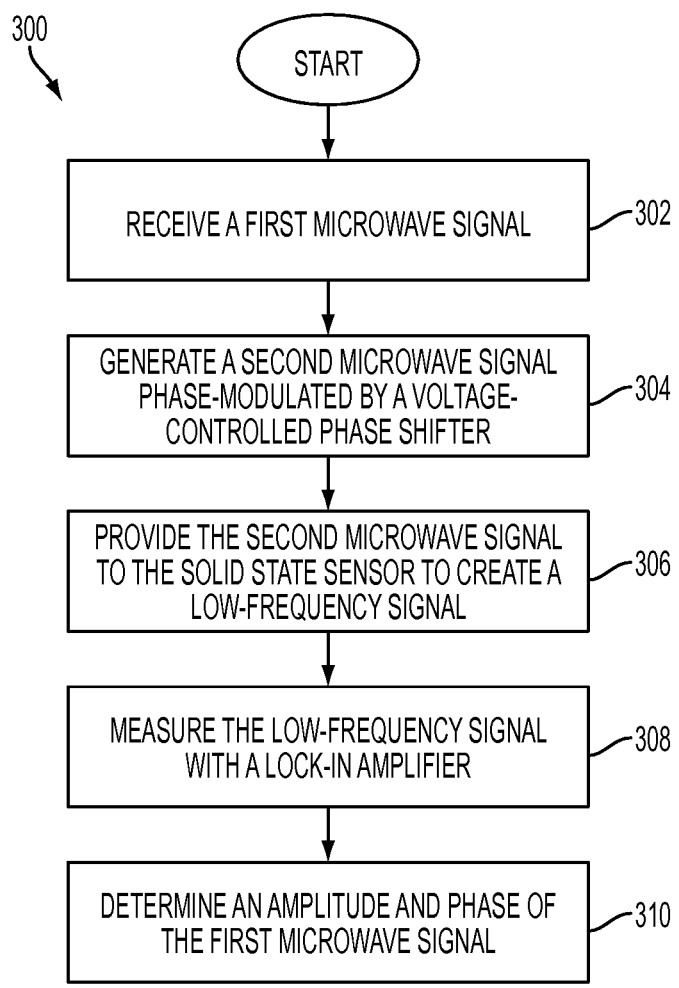
FIG. 3 is a flow chart illustrating a method of measuring microwave signals with a solid state sensor according to one embodiment of the disclosure.

FIG. 3 is a flow chart illustrating a method of measuring microwave signals with a solid state sensor according to one embodiment of the disclosure. A method 300 begins at block 302 with receiving a first microwave signal at a solid state sensor. The solid state sensor may include, for example, a magnetic tunnel junction (MTJ), a Schottky diode, and/or a metal-insulator-metal (MIM) diode. Then, at block 304, a second microwave signal may be generated by phase modulating the microwave signal from path 202B with a voltage-controlled phase shifter. At block 306, the combination of the first and second microwave signals creates a low frequency signal as described above. The signal generated by the solid state sensor may have an amplitude proportional to an amplitude of the first microwave signal and a phase having a defined relationship with the phase of the first microwave signal. At block 308, the low frequency signal may be measured with a lock-in amplifier to determine phase and/or amplitude information of the first microwave signal. At block 310, an amplitude and/or phase of the first microwave signal may be determined from a voltage measured across the solid state sensor at block 308. The determined amplitude and phase of the first microwave signal may be used to produce digital videos and/or photographs of the first microwave signal. In some embodiments, arrays of solid state sensors may be used to measure the first microwave signal at a plurality of points to construct the videos and/or photographs. Rapid phase measurements, such as through the method 300 of FIG. 3, may enable parallel sensing using arrays of solid state sensor.

According to one embodiment, through mixing of the first microwave signal and the second microwave signal, the measured microwave phase may be the phase shift between $\vec{e}$ waves. In another embodiment, the measured microwave phase may be the phase shift between $\vec{h}$ waves. In a further embodiment, the measured microwave phase may be the relative phase between the $\vec{e}$ wave and the $\vec{h}$ wave of the first microwave signal.

Figure 4A:
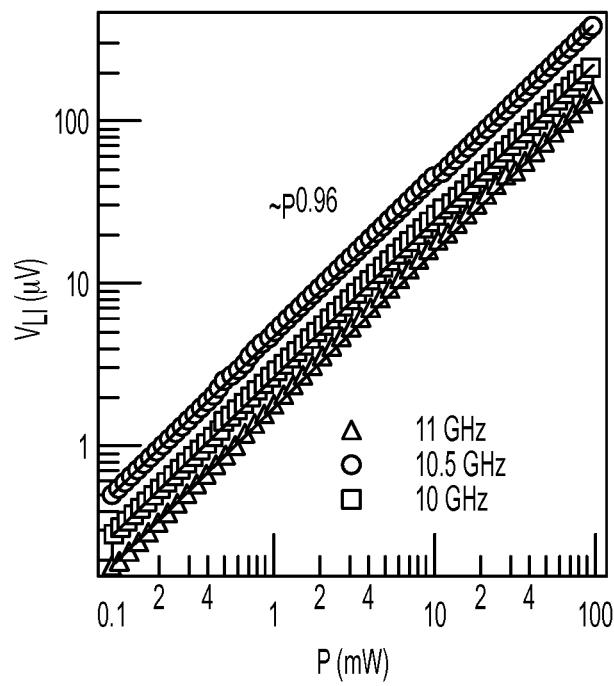
FIGS. 4A-B are graphs illustrating measured amplitude and phase from a solid state sensor of a microwave signal in one test according to one embodiment of the disclosure.
Figure 4B:
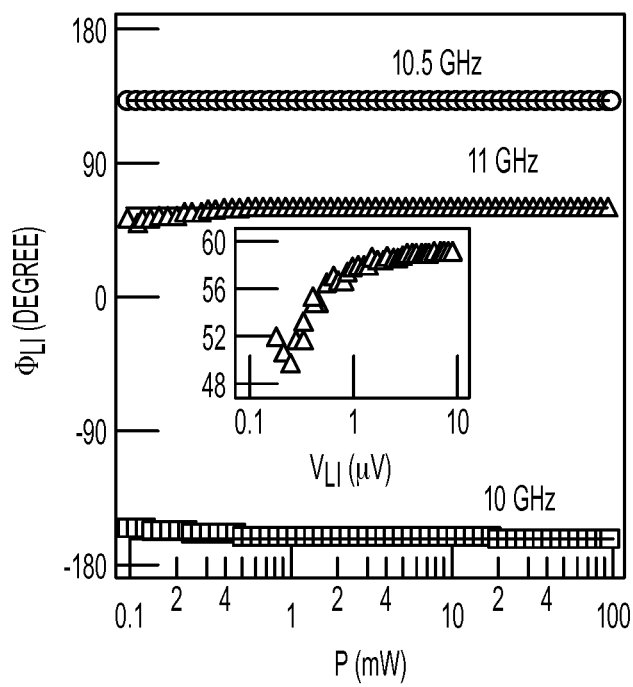

Results of detection of a microwave signal as described above are shown in FIGS. 4A-4B. These results were generated from experiments performed with a magnetic tunnel junction (MTJ) solid state sensor measuring a microwave signal. FIGS. 4A-B are graphs illustrating measured amplitude and phase, respectively, from a solid state sensor of a microwave signal in one test according to one embodiment of the disclosure. FIG. 4A illustrates a measured amplitude of a voltage from the MTJ at various power levels and various microwave signal frequencies. The voltage measured from the MTJ is approximately linear with respect to the power of the first microwave signal. FIG. 4B illustrates a measured phase of the signal from the MTJ at various power levels and various microwave frequencies. The measured phase may be relatively insensitive to the power level for a given frequency.

Figure 4C:
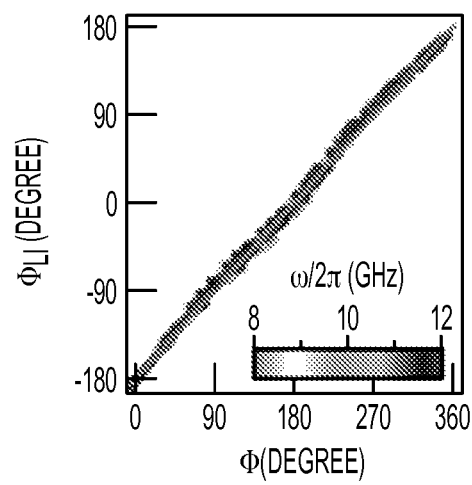
FIGS. 4C-D are graphs illustrating measured amplitude and phase from a solid state sensor of a microwave signal in a second test according to one embodiment of the disclosure.
Figure 4D:
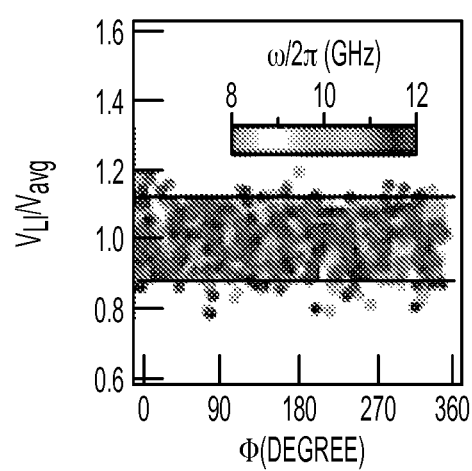

FIGS. 4C-D are graphs illustrating measured amplitude and phase from a solid state sensor of a microwave signal in a second test according to one embodiment of the disclosure. A mechanical phase shifter may be inserted in the path 404A and the phase of the first microwave signal varied and compared to the measured phase at the solid state sensor. FIG. 4C illustrates a measured phase of a voltage from the MTJ at various inserted phase shifts in the path 404A and at various power levels. The measured phase is approximately linear with inserted phase. FIG. 4D illustrates a measured amplitude of a voltage from the MTJ at various power levels and various frequencies. The measured amplitude may be relatively insensitive to the inserted phase in path 404A at many or all frequencies and power levels.

Figure 5:
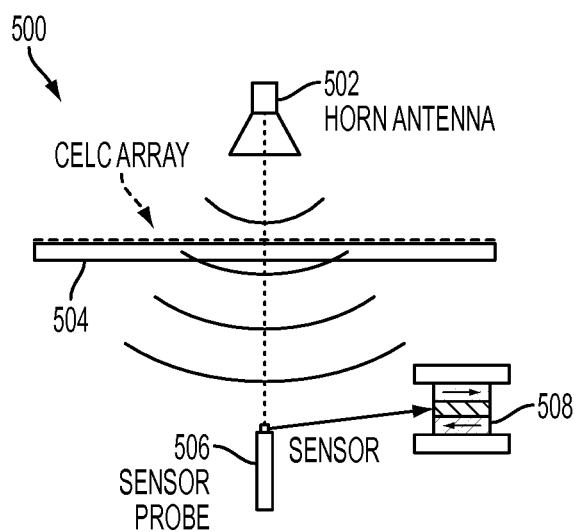
FIG. 5 is a block diagram illustrating a measurement of a complimentary electric inductive-capacitive (CELC) array with a solid state sensor according to one embodiment of the disclosure.

In one embodiment, the measurement apparatus and method described above in FIGS. 2 and 3, may be used to measure a complimentary electric inductive-capacitive (CELC) array. FIG. 5 is a block diagram illustrating a measurement of a CELC array with a solid state sensor according to one embodiment of the disclosure. A microwave signal may be transmitted from a horn antenna 502 through a CELC array 504 in a system 500. A sensor probe 506, including a solid state sensor such as a magnetic tunnel junction (MTJ) 508, may measure the microwave signal after passing through the CELC array 504. Measurements may be taken of the microwave signal with the solid state sensor 508 according to, for example, the method 300 of FIG. 3 and compared with measurements from a conventional measurement technique including a vector network analyzer (VNA).

Figure 6A:
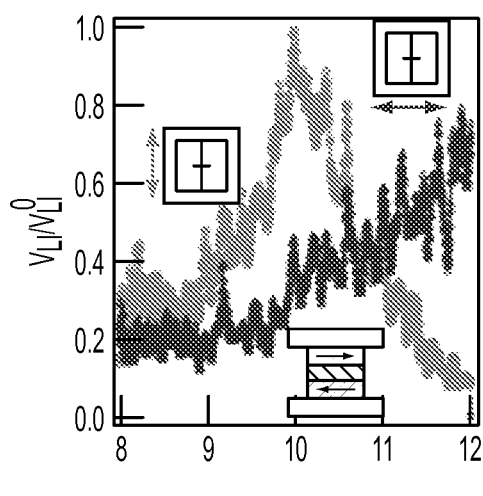
FIGS. 6A-B are graphs illustrating measured amplitude of a microwave signal passing through a CELC array from a solid state sensor according to one embodiment of the disclosure and a conventional antenna, respectively.
Figure 6B:
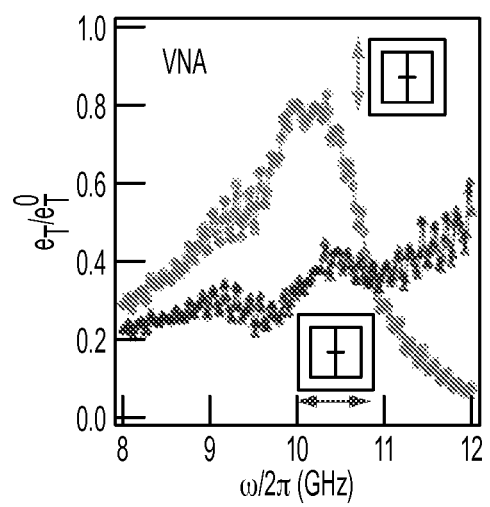

FIGS. 6A-B are graphs illustrating measured amplitude of a microwave signal from a solid state sensor according to one embodiment of the disclosure and a conventional antenna, respectively. FIG. 6A illustrates a measurement of amplitude of the microwave signal passing through a CELC array at various frequencies of microwave radiation with a solid state sensor according to one embodiment. The graph of FIG. 6A illustrates attenuation of microwave signals at various frequencies by the CELC array 504. FIG. 6B illustrates a measurement of amplitude of the microwave signal at various frequencies of microwave radiation with a conventional measurement technique. The graphs of FIGS. 6A and 6B demonstrate that the solid state sensor generates very similar results to that of the conventional measurement technique for amplitude of microwave signals.

Figure 7A:
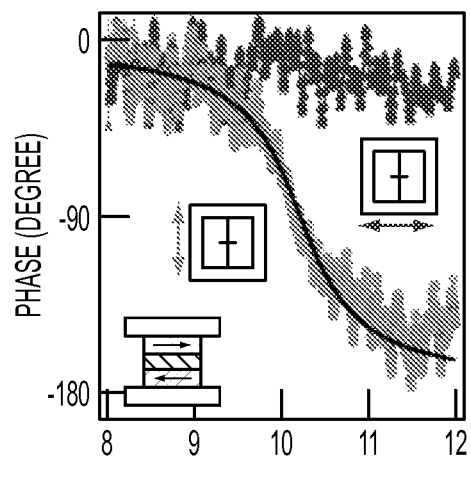
FIGS. 7A-B are graphs illustrating measured phase of a microwave signal passing through a CELC array from a solid state sensor according to one embodiment of the disclosure and a conventional antenna, respectively.
Figure 7B:
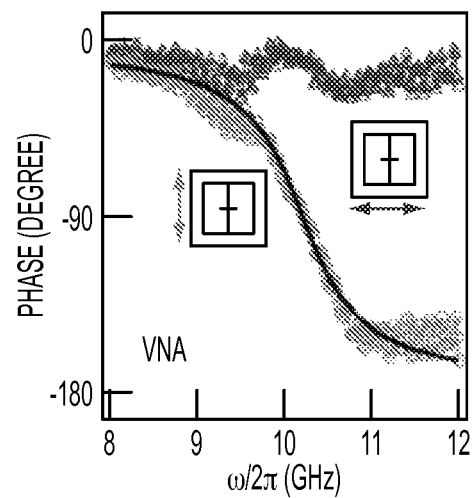

FIGS. 7A-B are graphs illustrating measured phase of a microwave signal passing through a CELC array from a solid state sensor according to one embodiment of the disclosure and a conventional antenna, respectively. FIG. 7A illustrates a measurement of phase of the microwave signal at various frequencies of microwave radiation with a solid state sensor according to one embodiment. The graph of FIG. 7A illustrates phase shift of microwave signals at various frequencies by the CELC array 504. FIG. 7B illustrates a measurement of phase of the microwave signal at various frequencies of microwave radiation with a conventional measurement technique. The graphs of FIGS. 7A and 7B demonstrate that the solid state sensor generates very similar results to that of the conventional measurement technique for phase of microwave signals.

Measurement of amplitude and phase information of microwave signals with solid state sensors, such as in the apparatus of FIG. 2 and the method of FIG. 3, allow quicker measurements of microwave signals than conventional techniques. For example, the solid state sensors may measure a range of frequencies without mechanically tuning the phase shifter. Furthermore, the use of solid state sensors reduces the cost of equipment for measuring microwave signals. Additionally, the solid state sensors allow for construction of smaller measurement devices, because antennas of conventional measurement systems have a size proportional to the frequency of the microwave signals. Furthermore, the crosstalk patterns of conventional antenna systems may not be present, or may be significantly reduced, in solid state sensors.

Measurement apparatuses and techniques for microwave signals may allow integrated sensors to non-contactively and non-destructively characterize engineered structures, such as metamaterials. The apparatuses and techniques may also be applied in biomedicine, security services, and civil engineering. For example, in a medical application the solid state sensors and measurement techniques may be used in early-stage cancer detection. In another example, in an anti-terrorism application the solid state sensors and measurement techniques may be used for detecting explosives. In other examples, the solid state sensors and measurement techniques may be used to perform ground penetrating detection and other non-destructive detection.

The methods described above, such as in FIG. 3, may be implemented in computer software or firmware. Likewise, the methods may be implemented as instructions to configure a processor to perform the various steps and functions.

If implemented in firmware and/or software, the functions described above may be stored as one or more instructions or code on a computer-readable medium. Examples include non-transitory computer-readable media encoded with a data structure and computer-readable media encoded with a computer program. Computer-readable media includes physical computer storage media. A storage medium may be any available medium that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to store desired program code in the form of instructions or data structures and that can be accessed by a computer. Disk and disc includes compact discs (CD), laser discs, optical discs, digital versatile discs (DVD), floppy disks and blu-ray discs. Generally, disks reproduce data magnetically, and discs reproduce data optically. Combinations of the above should also be included within the scope of computer-readable media.

In addition to storage on computer readable medium, instructions and/or data may be provided as signals on transmission media included in a communication apparatus. For example, a communication apparatus may include a transceiver having signals indicative of instructions and data. The instructions and data are configured to cause one or more processors to implement the functions outlined in the claims.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present invention, disclosure, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. An apparatus, comprising:
   a solid state sensor configured to receive a first microwave signal and a phase-modulated second microwave signal;
   a voltage-controlled phase shifter coupled to the solid state sensor and configured to provide the phase-modulated second microwave signal;
   a function generator coupled to the voltage-controlled phase shifter; and
   a lock-in amplifier coupled to the solid state sensor and configured to measure the first microwave signal.

2. The apparatus of claim 1, in which the solid state sensor comprises at least one of a conductor, a semiconductor, and an insulator.

3. The apparatus of claim 1, in which the solid state sensor comprises multiple layers.

4. The apparatus of claim 1, in which the solid state sensor comprises at least one of a magnetic tunnel junction (MTJ), a Schottky diode, a metal-insulator-metal (MIM) diode, and a solid state device that can rectify microwave signals.

5. The apparatus of claim 1, in which the first microwave signal corresponds to an electric field at the solid state sensor.

6. The apparatus of claim 1, in which the solid state sensor is configured to convert the first microwave signal received at the solid state sensor to at least one of low-frequency voltage signal and a low-frequency current signal, and in which the lock-in amplifier measures characteristics of the first microwave signal by measuring the low-frequency signal.

7. The apparatus of claim 6, in which the combination of the first microwave signal and the second microwave signal at the solid state sensor generates a low frequency signal having an amplitude proportional to an amplitude of the first microwave signal and having a phase with a defined relationship with the first microwave signal.

8. The apparatus of claim 7, in which the combination of the first microwave signal and the second microwave signal at the solid state sensor generates a voltage proportional to $$[e_T e_R \cos(2\omega t + \omega_r t + \varphi + \varphi_0) + e_T e_R \cos(\omega_r t + \varphi_0 - \varphi)]/2,$$

where $e_T$ is the first microwave signal and where $e_R$ is the second microwave signal.

9. The apparatus of claim 8, in which the voltage signal due to the mixing microwaves comprises a low frequency signal carrying phase information for the first microwave signal.

10. The apparatus of claim 9, in which the phase information for the first microwave signal is time-dependent.

11. The apparatus of claim 9, in which the lock-in amplifier is configured to detect in-phase and quadrature components of the voltage at the solid state sensor.

12. The apparatus of claim 1, in which the function generator is configured to generate a sawtooth wave.

13. The apparatus of claim 12, in which the lock-in amplifier is triggered by a square wave synchronized to the function generator.

14. The apparatus of claim 1, in which the apparatus comprises a microwave imaging system.

15. A method, comprising:
   receiving a first microwave signal at a solid state sensor;
   generating a second microwave signal phase-modulated by a voltage-controlled phase shifter;
   providing the second microwave signal to the solid state sensor to create a phase-modulated signal, in which the combination of the first microwave signal and the second microwave signal at the solid state sensor generates a low-frequency signal having an amplitude proportional to an amplitude of the first microwave signal and having a phase with a defined relationship with the first microwave signal; and measuring the low-frequency signal at the solid state sensor with a lock-in amplifier.

16. The method of claim 15, further comprising:
generating a sawtooth waveform;
providing the sawtooth waveform to the voltage-controlled phase shifter; and
triggering the lock-in amplifier with a square wave synchronized with the sawtooth waveform.

17. The method of claim 15, wherein the step of receiving comprises receiving the first microwave signal at the solid state sensor, in which the solid state sensor comprises at least one of a magnetic tunnel junction (MTJ), a Schottky diode, a metal-insulator-metal (MIM) diode, and a solid state device that rectifies microwave signals.

18. The method of claim 15, further comprising processing the measured low-frequency signal to produce an image of the first microwave signal.

19. A system, comprising:
an array of solid state sensors configured to receive a first microwave signal and a second microwave signal;
a lock-in amplifier coupled to the array of solid state sensors;
a voltage-controlled phase shifter coupled to the solid state sensors and configured to provide the second microwave signal; and
a function generator coupled to the voltage-controlled phase shifter.

20. The system of claim 19, wherein the array of solid state sensors comprise an array of at least one of magnetic tunnel junctions (MTJ), Schottky diodes, metal-insulator-metal (MIM) diodes, and solid state devices that rectify microwave signals.

21. The system of claim 19, in which the first microwave signal combined with the second microwave signal at the solid state sensor generates a low-frequency signal having an amplitude proportional to an amplitude of the first microwave signal and having a phase with a defined relationship with the first microwave signal.

22. The system of claim 19, wherein the array of solid state sensors are configured to perform medical imaging.

23. The system of claim 19, wherein the array of solid state sensors are configured to perform ground penetrating detection.

24. The system of claim 19, wherein the array of solid state sensors are configured to perform non-destructive testing.

* * * * *